United States Patent [19]

Huber et al.

[11] 4,088,446
[45] May 9, 1978

[54] METHOD AND APPARATUS FOR CLEANSING RESIDUE FROM A SAMPLE TRANSFER PROBE

[75] Inventors: Bernhard Werner Huber, Uberlingen; Rolf Günther Arnold Tamm, Salem, both of Germany

[73] Assignee: Bodenseewerk Perkin-Elmer & Co., GmbH, Uberlingen, Germany

[21] Appl. No.: 797,370

[22] Filed: May 16, 1977

[30] Foreign Application Priority Data

May 25, 1976 Germany .............................. 2623307

[51] Int. Cl.² ............................................. G01N 1/14
[52] U.S. Cl. .................................... 23/230 R; 23/259; 21/2; 134/19; 134/105
[58] Field of Search .................... 23/253 R, 259, 292, 23/230 R; 134/19, 105; 21/2

[56] References Cited

U.S. PATENT DOCUMENTS 3,536,449  10/1970  Astle .................................. 23/253 X
3,883,305  5/1975   Hoskins et al. ...................... 23/259 X
3,985,508  10/1976  Williams ............................. 23/259 X

*Primary Examiner*—R.E. Serwin
*Attorney, Agent, or Firm*—S. A. Giarratana; F. L. Masselle; E. T. Grimes

[57] ABSTRACT

Heat is applied to atomize the residual liquid from a sample transfer probe on which at least the tip is fabricated of heat resistant material. In one embodiment, the sample transfer probe is disposed within an atomic absorbtion spectrometer having a hollow graphite furnace that includes a port through which the sample is dispensed for atomization in the furnace. The probe tip in this embodiment is configured to extend into the graphite furnace while making thermal contact therewith so that the sample residue on the probe tip is atomized simultaneously with the sample in the furnace. Inert gas is connected to the sample transfer probe through a control valve to flush the atomized sample residue from within the probe tip in still another embodiment.

8 Claims, 1 Drawing Figure

U.S.Patent May 9, 1978 4,088,446
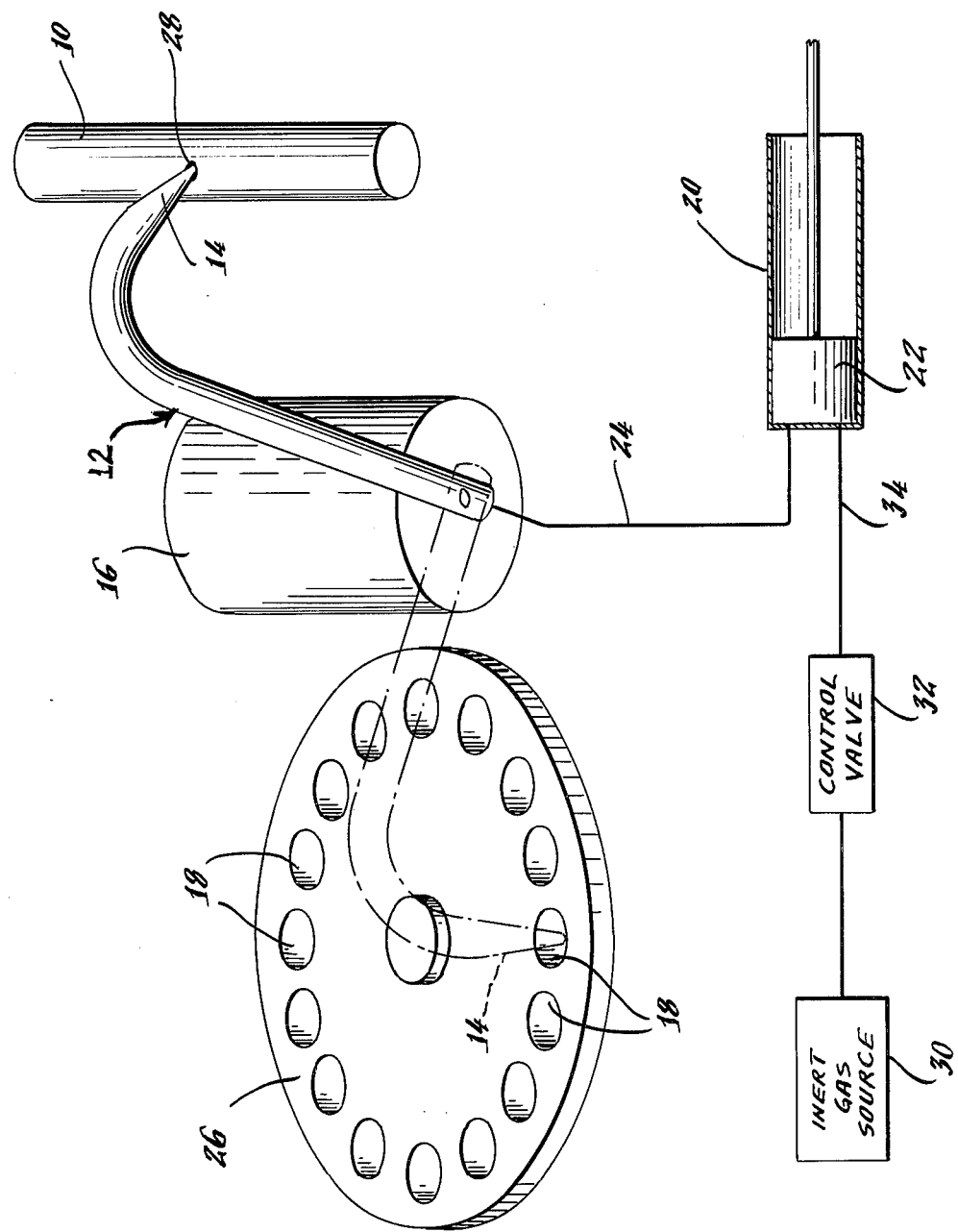

METHOD AND APPARATUS FOR CLEANSING RESIDUE FROM A SAMPLE TRANSFER PROBE

BACKGROUND OF THE INVENTION

The present invention relates to the cleansing of residue from sample transfer probes within analytical instruments so that the measurement error otherwise caused by cross-contamination between individual samples is avoided. Such cleansing is commonly accomplished in prior art instruments by flushing the probe both interiorly and exteriorly with a suitable non-contaminating liquid. Because of this flushing procedure, prior art instruments must include pumps, valves and containers for the flushing liquid which add to the design complexity and expense of such instruments.

SUMMARY OF THE INVENTION

It is the object of this invention to provide both a method and apparatus for cleansing residue from sample transfer probes within analytical instruments without using a flushing liquid.

These objects are accomplished in accordance with the present invention by fabricating at least the tip of the sample transfer probe from a heat resistant material and heating the probe tip to atomize the sample residue therefrom after each sample transfer to the test chamber of the analytical instrument. In one embodiment where the analytical instrument is an atomic absorbtion spectrometer, the probe tip is configured to extend into a graphite furnace while making thermal contact therewith during the cleansing period. A source of inert gas is connected to flush the probe tip in still another atomic absorbtion spectrometer embodiment.

BRIEF DESCRIPTION OF THE DRAWING

The manner in which these and other objects of the present invention are achieved will be understood from the following description, the appended claims, and the attached drawing wherein:

FIG. 1 is a mechanical schematic of a sample transfer probe in an atomic absorbtion spectrometer with the probe tip cleansing apparatus of this invention incorporated therein.

DESCRIPTION OF THE PREFERRED EMBODIMENTS

As provided by this invention, the method of cleansing residue from sample transfer probes within analytical instruments is accomplished by fabricating at least the tip of the probe from heat resistant material and by heating the probe tip to atomize the residue therefrom after each sample transfer to the test chamber of the instrument. Depending on the chemical and physical properties of the samples to be transferred, many heat resistant materials can be utilized for the probe tip. Some heat resistant materials that have been found suitable where atomization of the samples occur at very high temperatures are graphite, glass-like carbon, tantalum, and tungsten. Of course, glass-like carbon is commonly manufactured by the carbonization and subsequent heat-treatment of organic substances having strong molecular polymerization. Furthermore, the probe tip may be heated in any conventional manner to atomize the sample residue therefrom, such as to locate the probe tip in a flame or oven. It should be understood without further explanation that the probe tip must be allowed to cool between each sample transfer.

Because no flushing liquid is required with the probe tip residue cleansing method of this invention, reductions in the design complexity and expense are realized from the incorporation of this cleansing method into analytical instruments. Such reductions are derived from the elimination of the pumps, valves, and containers that are otherwise necessary where a flushing liquid is utilized in analytical instruments to cleanse residue from sample transfer probes.

Many analytical instruments utilize sample transfer probes, such as chromatographs and spectrometers. The typical sample transfer probe apparatus for an atomic absorption spectrometer is illustrated in FIG. 1 where a graphite furnace 10 is utilized as the test chamber of this instrument. A probe 12 having a tip 14 is maneuvered from a motor 16 between an intake position at sample containers 18 (shown by phantom lines) and a discharge position at the graphite furnace 10. A metering pump 20 having a displaceable piston 22 is connected to the probe 12 through a conduit 24 and is conventionally programmed to operate at the intake and discharge positions of the probe 12 as part of the spectrometer. The sample containers 18 are peripherally disposed around a turntable 26 which is conventionally programmed to move in positioning the containers 18 as part of the spectrometer. Because the probe tip 14 is directed downward at both its intake and discharge positions, the probe 12 is turned about its longitudinal axis when maneuvering between those positions.

One apparatus embodiment of this invention is shown incorporated into the sample transport probe apparatus of FIG. 1 where the structural aspects of the graphite furnace 10 are not completely shown. Because the graphite furance 10 functions within the spectrometer to atomize the samples, it is tubularly shaped and has a port 28 through its tubular wall into which the probe tip 14 extends to discharge each sample. Electric power is periodically dissipated through the graphite furnace 10 to heat the tubular wall thereof up to the atomization temperature of the samples. At least the tip 14 of the probe 12 is fabricated from heat resistant material in the apparatus of this invention and means for heating the probe tip 14 is included therein to atomize the residue from the probe tip 14 after each sample transfer to the graphite furnace 10. Again, the probe tip must be allowed to cool between each sample transfer and many heat resistant materials can be utilized for the probe tip 14 such as graphite, glass-like carbon, tantalum, and tungsten. Although the heating means could include any conventional source of heat such as a flame or an oven, in FIG. 1 the probe tip 14 is configured to make thermal contact with the graphite furnace 10 when it is extended into the port 28. Then heat is conducted to the probe tip 14 from the graphite furnace 10 while each dispensed sample is being atomized therein until the probe tip 14 reaches the atomization temperature of the residue thereon. Of course, the manipulations of the probe 12 are conventionally sequenced by a programmer (not shown) and include a dwell period at the discharge position thereof.

The sample transfer probe apparatus of FIG. 1 also illustrates another apparatus embodiment of this invention wherein a source 30 of inert gas is connected to the metering pump 20 through a control valve 32 by a conduit 34. The control valve 32 is sequenced by the previously mentioned programmer to purge any air from the probe 12 before the intake position is assumed thereby and to expel the sample residue, as well as the atomized form thereof, while the discharge position is assumed by the probe 12. By purging any air from the probe 12 before the intake position is assumed thereby, it is insured that no air is blown into the graphite furnace 10 when the sample is discharged therein. The flow of inert gas through the probe 12 while it is at the discharge position precludes any of the atomized sample from diffusing back into the probe 12 toward the cooler wall portions thereof where it would become condensed. Furthermore, this flow inhibits any interior oxidation of the probe 12 near the atomization temperature of the sample while it is located at the discharge position.

Although this invention has been disclosed herein by describing only one method and a few apparatus embodiments thereof, it should be understood by those skilled in the art that numerous changes in the details of construction and the combination or arrangement of parts could be made in the described method or apparatus embodiments without departure from the true scope and spirit of the invention. Therefore, the present disclosure should be construed as illustrative rather than limiting.

What we claim is:

1. In an atomic absorption spectrometer of the type wherein a probe is automated to transfer samples between individual sample containers and a hollow graphite furnace in which each transferred sample is atomized, a method of cleansing sample residue from the probe comprising the steps of:

bringing the tip of the probe into thermal contact with the graphite furnace at the sample transfer position of the probe to heat the probe tip to atomize the sample residue therefrom after each sample transfer to the graphite furnace.

2. The method of claim 1 further comprising the step of:

passing an inert gas through said probe to flush air and atomized sample therefrom.

3. In an atomic absorption spectrometer of the type wherein a probe is automated to transfer samples between individual sample containers and a hollow graphite furnace in which each transferred sample is atomized, the improvement comprising:

at least the tip of the probe being fabricated from heat-resistant material, the probe tip being configured to extend into the graphite furnace while making thermal contact therewith at the sample transfer position of the probe and the automation of the probe including a dwell period at the transfer position of the probe to heat the probe tip to atomize the sample residue therefrom after each sample transfer to the graphite furnace.

4. The combination of claim 3 wherein a source of inert gas is connected to the probe through a control valve to flush air and atomized sample therefrom.

5. The combination of claim 3 wherein the heat resistant material of the probe tip is graphite.

6. The combination of claim 3 wherein the heat resistant material of the probe tip is glass-like carbon.

7. The combination of claim 3 wherein the heat resistant material of the probe tip is tantalum.

8. The combination of claim 3 wherein the heat resistant material of the probe tip is tungsten.

* * * * *